(12) United States Patent
Hallisey et al.

(10) Patent No.: US 11,116,483 B2
(45) Date of Patent: Sep. 14, 2021

(54) ROTATING BIOPSY NEEDLE

(71) Applicant: Merit Medical Systems, Inc., South Jordan, UT (US)

(72) Inventors: Denise Hallisey, Wethersfield, CT (US); Mark DeBisschop, Harwinton, CT (US)

(73) Assignee: Merit Medical Systems, Inc., South Jordan, UT (US)

(*) Notice: Subject to any disclaimer, the term of this patent is extended or adjusted under 35 U.S.C. 154(b) by 250 days.

(21) Appl. No.: 15/982,624

(22) Filed: May 17, 2018

(65) Prior Publication Data
US 2018/0333146 A1 Nov. 22, 2018

Related U.S. Application Data

(60) Provisional application No. 62/508,882, filed on May 19, 2017.

(51) Int. Cl.
*A61B 10/02* (2006.01)
*A61B 8/08* (2006.01)
*A61B 17/34* (2006.01)

(52) U.S. Cl.
CPC ........ *A61B 10/0275* (2013.01); *A61B 8/0841* (2013.01); *A61B 8/481* (2013.01); *A61B 17/3421* (2013.01); *A61B 2010/0225* (2013.01); *A61B 2017/3413* (2013.01)

(58) Field of Classification Search
CPC ........ A61B 10/0275; A61B 2010/0225; A61B 8/0841; A61B 8/481; A61B 17/3421; A61B 2017/3413
See application file for complete search history.

(56) References Cited

U.S. PATENT DOCUMENTS

| | | |
|---|---|---|
| 737,293 A | 8/1903 | Summerfeldt |
| 1,585,934 A | 12/1923 | Muir |
| 1,663,761 A | 2/1927 | Johnson |
| 2,953,934 A | 9/1960 | Sundt |
| 3,019,733 A | 2/1962 | Braid |
| 3,224,434 A | 12/1965 | Molomut et al. |
| 3,477,423 A | 11/1969 | Griffith |
| 3,512,519 A | 5/1970 | Hall |

(Continued)

FOREIGN PATENT DOCUMENTS

| | | |
|---|---|---|
| DE | 2848314 | 10/1979 |
| DE | 3924291 | 1/1991 |

(Continued)

OTHER PUBLICATIONS

International Search Report and Written Opinion dated Jul. 2, 2009 for PCT/KR2009/006741.

(Continued)

*Primary Examiner* — Devin B Henson
(74) *Attorney, Agent, or Firm* — Stoel Rives LLP

(57) ABSTRACT

A biopsy needle assembly configured for use with a tissue biopsy device is disclosed. The biopsy needle assembly may be configured to be advanced to a predetermined tissue sample, sever the tissue sample, and extract the tissue sample from a body tissue of a patient. The biopsy needle assembly may be further configured to minimize or eliminate the axial translation of the biopsy needle beyond a targeted location.

20 Claims, 8 Drawing Sheets

(56) References Cited

U.S. PATENT DOCUMENTS

| | | |
|---|---|---|
| 3,561,429 A | 2/1971 | Jewett et al. |
| 3,565,074 A | 2/1971 | Foti |
| 3,606,878 A | 9/1971 | Kellogg |
| 3,727,602 A | 4/1973 | Hayden et al. |
| 3,732,858 A | 5/1973 | Banko |
| 3,800,783 A | 4/1974 | Jamshidi |
| 3,844,272 A | 10/1974 | Banko |
| 3,882,849 A | 5/1975 | Jamshidi |
| 4,275,730 A | 6/1981 | Hussein |
| 4,282,884 A | 8/1981 | Boebel |
| 4,306,570 A | 12/1981 | Matthews |
| 4,354,092 A | 10/1982 | Manabe et al. |
| 4,445,509 A | 5/1984 | Auth |
| 4,490,137 A | 12/1984 | Moukheibir |
| 4,549,554 A | 10/1985 | Markham |
| 4,557,265 A | 12/1985 | Anderson |
| 4,577,629 A | 3/1986 | Martinez |
| 4,589,414 A | 5/1986 | Yoshida et al. |
| 4,598,710 A | 7/1986 | Kleinberg et al. |
| 4,603,694 A | 8/1986 | Wheeler |
| 4,605,011 A | 8/1986 | Naslund |
| 4,617,430 A | 10/1986 | Bryant |
| 4,620,539 A | 11/1986 | Andrews et al. |
| 4,643,197 A | 2/1987 | Greene et al. |
| 4,645,153 A | 2/1987 | Granzow et al. |
| 4,662,869 A | 5/1987 | Wright |
| 4,678,459 A | 7/1987 | Onik et al. |
| 4,683,885 A | 8/1987 | Hutterer et al. |
| 4,696,298 A | 9/1987 | Higgins et al. |
| 4,702,260 A | 10/1987 | Wang |
| 4,708,147 A | 11/1987 | Haaga |
| 4,776,346 A | 10/1988 | Beraha et al. |
| 4,844,087 A | 7/1989 | Garg |
| 4,850,354 A | 7/1989 | McGurk-Burleson et al. |
| 4,893,635 A | 1/1990 | De Groot et al. |
| 4,907,598 A | 3/1990 | Bauer |
| RE33,258 E | 7/1990 | Onik et al. |
| 4,940,061 A | 7/1990 | Terwilliger et al. |
| 4,952,817 A | 8/1990 | Bolan et al. |
| 4,958,625 A | 9/1990 | Bates et al. |
| 4,967,762 A | 11/1990 | Devries |
| 4,986,278 A | 1/1991 | Ravid et al. |
| 4,986,279 A | 1/1991 | O'Neill |
| 4,986,807 A | 1/1991 | Farr |
| 4,989,614 A | 2/1991 | Dejter, Jr. et al. |
| 5,025,797 A | 6/1991 | Baran |
| 5,125,413 A | 6/1992 | Baran |
| 5,138,245 A | 8/1992 | Mattinger et al. |
| 5,146,921 A | 9/1992 | Terwilliger et al. |
| 5,158,528 A | 10/1992 | Walker et al. |
| 5,176,628 A | 1/1993 | Charles et al. |
| 5,225,763 A | 7/1993 | Krohn et al. |
| 5,226,910 A | 7/1993 | Kajiyama et al. |
| 5,234,000 A | 8/1993 | Hakky et al. |
| 5,236,334 A | 8/1993 | Bennett |
| 5,249,583 A | 10/1993 | Mallaby |
| 5,269,791 A | 12/1993 | Mayzels et al. |
| 5,282,476 A | 2/1994 | Terwilliger |
| 5,282,477 A | 2/1994 | Bauer |
| 5,284,472 A | 2/1994 | Sussman et al. |
| 5,292,327 A | 3/1994 | Dodd et al. |
| 5,324,306 A | 6/1994 | Makower et al. |
| 5,334,183 A | 8/1994 | Wuchinich |
| 5,336,229 A | 8/1994 | Noda |
| 5,368,029 A | 11/1994 | Holcombe et al. |
| 5,368,045 A | 11/1994 | Clement et al. |
| 5,395,313 A | 3/1995 | Naves et al. |
| 5,400,798 A | 3/1995 | Baran |
| 5,409,013 A | 4/1995 | Clement |
| 5,439,474 A | 8/1995 | Li |
| 5,441,510 A | 8/1995 | Simpson et al. |
| 5,458,112 A | 10/1995 | Weaver |
| 5,469,860 A | 11/1995 | De Santis |
| 5,479,486 A | 12/1995 | Saji |
| 5,485,917 A | 1/1996 | Early |
| 5,492,130 A | 2/1996 | Chiou |
| 5,505,210 A | 4/1996 | Clement |
| 5,511,556 A | 4/1996 | De Santis |
| 5,526,822 A | 6/1996 | Burbank et al. |
| 5,527,322 A | 6/1996 | Clement |
| 5,535,755 A | 7/1996 | Heske |
| 5,546,957 A | 8/1996 | Heske |
| 5,554,151 A | 9/1996 | Hinchliffe |
| 5,560,373 A | 10/1996 | De Santis |
| 5,562,685 A | 10/1996 | Mollenauer et al. |
| 5,564,436 A | 10/1996 | Hakky et al. |
| 5,569,277 A | 10/1996 | Evans et al. |
| 5,569,284 A | 10/1996 | Young et al. |
| 5,575,293 A | 11/1996 | Miller et al. |
| 5,582,616 A | 12/1996 | Bolduc et al. |
| 5,591,170 A | 1/1997 | Speivack et al. |
| 5,601,585 A | 2/1997 | Banik et al. |
| 5,602,449 A | 2/1997 | Krause et al. |
| 5,617,874 A | 4/1997 | Baran |
| 5,643,304 A | 7/1997 | Schechter et al. |
| 5,649,547 A | 7/1997 | Ritchart et al. |
| 5,655,542 A | 8/1997 | Weilandt |
| 5,655,657 A | 8/1997 | Roshdy |
| 5,665,101 A | 9/1997 | Becker et al. |
| 5,669,394 A | 9/1997 | Bergey |
| 5,699,909 A | 12/1997 | Foster |
| 5,700,265 A | 12/1997 | Romano |
| 5,709,697 A | 1/1998 | Ratcliff et al. |
| 5,720,760 A | 2/1998 | Becker et al. |
| 5,735,264 A | 4/1998 | Siczek et al. |
| 5,752,923 A | 5/1998 | Terwilliger |
| 5,755,714 A | 5/1998 | Murphy-Chutorian |
| 5,766,135 A | 6/1998 | Terwilliger |
| 5,769,086 A | 6/1998 | Ritchart et al. |
| 5,769,795 A | 6/1998 | Terwilliger |
| 5,775,333 A | 7/1998 | Burbank et al. |
| 5,788,651 A | 8/1998 | Weilandt |
| 5,792,167 A | 8/1998 | Kablik et al. |
| 5,807,282 A | 9/1998 | Fowler |
| 5,817,033 A | 10/1998 | De Santis et al. |
| 5,817,034 A | 10/1998 | Milliman et al. |
| 5,823,970 A | 10/1998 | Terwilliger |
| 5,827,305 A | 10/1998 | Gordon |
| 5,830,219 A | 11/1998 | Bird et al. |
| D403,405 S | 12/1998 | Terwilliger |
| 5,857,982 A | 1/1999 | Milliman et al. |
| 5,879,365 A | 3/1999 | Whitfield et al. |
| 5,908,233 A | 6/1999 | Heskett et al. |
| 5,913,857 A | 6/1999 | Ritchart et al. |
| 5,916,198 A | 6/1999 | Dillow |
| 5,916,229 A | 6/1999 | Evans |
| 5,928,164 A | 7/1999 | Burbank et al. |
| 5,944,673 A | 8/1999 | Gregoire et al. |
| 5,951,490 A | 9/1999 | Fowler |
| 5,951,575 A | 9/1999 | Bolduc et al. |
| 5,964,716 A | 10/1999 | Gregoire et al. |
| 5,971,939 A | 10/1999 | De Santis et al. |
| 5,976,164 A | 11/1999 | Bencini et al. |
| 5,980,469 A | 11/1999 | Burbank et al. |
| 5,980,545 A | 11/1999 | Pacala et al. |
| 6,007,495 A | 12/1999 | Matula |
| 6,007,497 A | 12/1999 | Huitema |
| 6,007,556 A | 12/1999 | Kablik et al. |
| 6,017,316 A | 1/2000 | Ritchart et al. |
| 6,018,227 A | 1/2000 | Kumar et al. |
| 6,019,733 A | 2/2000 | Farascioni |
| 6,022,324 A | 2/2000 | Skinner |
| 6,022,325 A | 2/2000 | Siczek et al. |
| 6,027,458 A | 2/2000 | Janssens |
| 6,036,657 A | 3/2000 | Milliman et al. |
| 6,050,955 A | 4/2000 | Bryan et al. |
| 6,077,230 A | 6/2000 | Gregoire et al. |
| 6,083,176 A | 7/2000 | Terwilliger |
| 6,083,237 A | 7/2000 | Huitema et al. |
| 6,086,544 A | 7/2000 | Hibner et al. |
| 6,106,484 A | 8/2000 | Terwilliger |
| 6,110,129 A | 8/2000 | Terwilliger |
| 6,120,462 A | 9/2000 | Hibner et al. |
| 6,123,957 A | 9/2000 | Jernberg |

(56) References Cited

U.S. PATENT DOCUMENTS

| | | |
|---|---|---|
| 6,126,617 A | 10/2000 | Weilandt et al. |
| 6,142,955 A | 11/2000 | Farascioni et al. |
| 6,162,187 A | 12/2000 | Buzzard et al. |
| 6,165,136 A | 12/2000 | Nishtala |
| 6,193,673 B1 | 2/2001 | Viola et al. |
| 6,196,978 B1 | 3/2001 | Weilandt et al. |
| 6,213,957 B1 | 4/2001 | Milliman et al. |
| 6,220,248 B1 | 4/2001 | Voegele et al. |
| 6,231,522 B1 | 5/2001 | Voegele et al. |
| 6,241,687 B1 | 6/2001 | Voegele et al. |
| 6,267,759 B1 | 7/2001 | Quick |
| 6,273,861 B1 | 8/2001 | Bates et al. |
| 6,273,862 B1 | 8/2001 | Privitera et al. |
| 6,280,398 B1 | 8/2001 | Ritchart et al. |
| 6,283,925 B1 | 9/2001 | Terwilliger |
| 6,322,523 B2 | 11/2001 | Weilandt et al. |
| 6,328,701 B1 | 12/2001 | Terwilliger |
| 6,331,166 B1 | 12/2001 | Burbank et al. |
| 6,358,217 B1 | 3/2002 | Bourassa |
| 6,361,504 B1 | 3/2002 | Shin |
| 6,402,701 B1 | 6/2002 | Kaplan et al. |
| 6,419,641 B1 | 7/2002 | Mark et al. |
| 6,428,486 B2 | 8/2002 | Ritchart et al. |
| 6,428,487 B1 | 8/2002 | Burdorff et al. |
| 6,432,064 B1 | 8/2002 | Hibner et al. |
| 6,432,065 B1 | 8/2002 | Burdorff et al. |
| 6,436,054 B1 | 8/2002 | Viola et al. |
| 6,482,158 B2 | 11/2002 | Mault |
| 6,485,436 B1 | 11/2002 | Truckai et al. |
| 6,488,636 B2 | 12/2002 | Bryan et al. |
| 6,527,736 B1 | 3/2003 | Attinger et al. |
| 6,540,694 B1 | 4/2003 | Van Bladel et al. |
| 6,540,761 B2 | 4/2003 | Houser |
| 6,551,255 B2 | 4/2003 | Van Bladel et al. |
| 6,554,779 B2 | 4/2003 | Viola et al. |
| 6,585,664 B2 | 7/2003 | Burdoff et al. |
| 6,585,694 B1 | 7/2003 | Smith et al. |
| 6,638,235 B2 | 10/2003 | Miller et al. |
| 6,656,133 B2 | 12/2003 | Voegele et al. |
| 6,659,105 B2 | 12/2003 | Burbank et al. |
| 6,659,338 B1 | 12/2003 | Dittmann et al. |
| 6,683,439 B2 | 1/2004 | Takano et al. |
| 6,689,072 B2 | 2/2004 | Kaplan et al. |
| 6,695,786 B2 | 2/2004 | Wang et al. |
| 6,712,773 B1 | 3/2004 | Viola |
| 6,712,774 B2 | 3/2004 | Voegele et al. |
| 6,752,768 B2 | 6/2004 | Burdorff et al. |
| 6,753,671 B1 | 6/2004 | Harvey |
| 6,758,824 B1 | 7/2004 | Miller et al. |
| 6,764,495 B2 | 7/2004 | Lee et al. |
| 6,832,990 B2 | 12/2004 | Kortenbach et al. |
| 6,849,080 B2 | 2/2005 | Lee et al. |
| 6,908,440 B2 | 6/2005 | Fisher |
| D508,458 S | 8/2005 | Solland et al. |
| 6,926,676 B2 | 8/2005 | Turturro et al. |
| 6,984,213 B2 | 1/2006 | Horner et al. |
| 7,025,732 B2 | 4/2006 | Thompson et al. |
| 7,048,694 B2 | 5/2006 | Mark et al. |
| D525,583 S | 7/2006 | Vu |
| 7,153,274 B2 | 12/2006 | Stephens et al. |
| 7,189,206 B2 | 3/2007 | Quick et al. |
| 7,189,207 B2 | 3/2007 | Viola |
| 7,219,867 B2 | 5/2007 | Kalis et al. |
| 7,226,424 B2 | 6/2007 | Ritchart et al. |
| 7,276,032 B2 | 10/2007 | Hibner et al. |
| 7,328,794 B2 | 2/2008 | Lubs et al. |
| 7,347,829 B2 | 3/2008 | Mark et al. |
| 7,374,544 B2 | 5/2008 | Freeman et al. |
| 7,397,654 B2 | 7/2008 | Mori |
| 7,402,140 B2 | 7/2008 | Spero et al. |
| 7,405,536 B2 | 7/2008 | Watts |
| 7,407,054 B2 | 8/2008 | Seiler et al. |
| 7,432,813 B2 | 10/2008 | Postma |
| 7,452,367 B2 | 11/2008 | Rassman et al. |
| 7,464,040 B2 | 12/2008 | Joao |
| 7,473,232 B2 | 1/2009 | Teague |
| 7,481,775 B2 | 1/2009 | Weikel, Jr. et al. |
| 7,490,048 B2 | 2/2009 | Joao |
| 7,513,877 B2 | 4/2009 | Viola |
| 7,517,321 B2 | 4/2009 | McCullough et al. |
| 7,517,322 B2 | 4/2009 | Weikel, Jr. et al. |
| 7,648,466 B2 | 1/2010 | Stephens et al. |
| 7,670,299 B2 | 3/2010 | Beckman et al. |
| 7,717,861 B2 | 5/2010 | Weikel et al. |
| 7,727,164 B2 | 6/2010 | Cicenas et al. |
| 7,740,594 B2 | 6/2010 | Hibner |
| 7,740,596 B2 | 6/2010 | Hibner |
| 7,740,597 B2 | 6/2010 | Cicenas et al. |
| 7,762,961 B2 | 7/2010 | Heske et al. |
| 7,828,746 B2 | 11/2010 | Teague |
| 7,854,706 B2 | 12/2010 | Hibner |
| 7,883,476 B2 | 2/2011 | Miller et al. |
| 8,251,917 B2 | 8/2012 | Almazan |
| 2001/0005778 A1 | 6/2001 | Ouchi |
| 2001/0007925 A1 | 7/2001 | Ritchart et al. |
| 2001/0011156 A1 | 8/2001 | Viola et al. |
| 2001/0012919 A1 | 8/2001 | Terwilliger |
| 2001/0014779 A1 | 8/2001 | Burbank et al. |
| 2001/0034530 A1 | 10/2001 | Malackowski et al. |
| 2001/0044595 A1 | 11/2001 | Reydel et al. |
| 2001/0047183 A1 | 11/2001 | Privitera et al. |
| 2002/0045840 A1 | 4/2002 | Voegele et al. |
| 2002/0065474 A1 | 5/2002 | Viola |
| 2002/0067151 A1 | 6/2002 | Tanishita |
| 2002/0068878 A1 | 6/2002 | Jasonni et al. |
| 2002/0077646 A1 | 6/2002 | Truwit et al. |
| 2002/0082518 A1 | 6/2002 | Weiss et al. |
| 2002/0107043 A1 | 8/2002 | Adamson et al. |
| 2002/0120212 A1 | 8/2002 | Ritchart et al. |
| 2002/0151822 A1 | 10/2002 | Brudorff et al. |
| 2002/0156395 A1 | 10/2002 | Stephens et al. |
| 2003/0114875 A1 | 6/2003 | Sjostrom |
| 2003/0130593 A1 | 7/2003 | Gonzalez |
| 2003/0130677 A1 | 7/2003 | Whitman et al. |
| 2003/0163142 A1 | 8/2003 | Paltieli et al. |
| 2003/0229293 A1 | 12/2003 | Hibner et al. |
| 2003/0233101 A1 | 12/2003 | Lubock et al. |
| 2004/0015079 A1 | 1/2004 | Berger et al. |
| 2004/0019297 A1 | 1/2004 | Angel |
| 2004/0030367 A1 | 2/2004 | Yamaki et al. |
| 2004/0049128 A1 | 3/2004 | Miller et al. |
| 2004/0054299 A1 | 3/2004 | Burdorff et al. |
| 2004/0092992 A1 | 5/2004 | Adams et al. |
| 2004/0167427 A1 | 8/2004 | Quick et al. |
| 2004/0186393 A1 | 9/2004 | Leigh et al. |
| 2004/0215103 A1 | 10/2004 | Mueller et al. |
| 2004/0220495 A1 | 11/2004 | Cahir et al. |
| 2004/0249278 A1 | 12/2004 | Krause |
| 2004/0267157 A1 | 12/2004 | Miller et al. |
| 2005/0004492 A1 | 1/2005 | Burbank et al. |
| 2005/0004559 A1 | 1/2005 | Quick et al. |
| 2005/0010131 A1 | 1/2005 | Burbank et al. |
| 2005/0020909 A1 | 1/2005 | Moctezuma De La Barrera et al. |
| 2005/0027210 A1 | 2/2005 | Miller |
| 2005/0049489 A1 | 3/2005 | Foerster et al. |
| 2005/0049521 A1 | 3/2005 | Miller et al. |
| 2005/0080355 A1 | 4/2005 | Mark |
| 2005/0085838 A1 | 4/2005 | Thompson et al. |
| 2005/0101879 A1 | 5/2005 | Shidham et al. |
| 2005/0113715 A1 | 5/2005 | Scwindt et al. |
| 2005/0113716 A1 | 5/2005 | Mueller, Jr. et al. |
| 2005/0124914 A1 | 6/2005 | Dicarlo et al. |
| 2005/0124915 A1 | 6/2005 | Eggers et al. |
| 2005/0165328 A1 | 7/2005 | Heske et al. |
| 2005/0177117 A1 | 8/2005 | Crocker et al. |
| 2005/0193451 A1 | 9/2005 | Quistgaard et al. |
| 2005/0203439 A1 | 9/2005 | Heske et al. |
| 2005/0209530 A1 | 9/2005 | Pflueger |
| 2005/0275378 A1 | 12/2005 | Canino et al. |
| 2005/0277829 A1 | 12/2005 | Tsonton et al. |
| 2005/0277871 A1 | 12/2005 | Selis |
| 2006/0030784 A1 | 2/2006 | Miller et al. |
| 2006/0074344 A1 | 4/2006 | Hibner |
| 2006/0074345 A1 | 4/2006 | Hibner |

(56) References Cited

U.S. PATENT DOCUMENTS

| | | |
|---|---|---|
| 2006/0074346 A1 | 4/2006 | Hibner |
| 2006/0113958 A1 | 6/2006 | Lobert et al. |
| 2006/0116603 A1 | 6/2006 | Shibazaki et al. |
| 2006/0129063 A1 | 6/2006 | Thompson et al. |
| 2006/0173377 A1 | 8/2006 | McCullough et al. |
| 2006/0178666 A1 | 8/2006 | Cosman et al. |
| 2006/0184063 A1 | 8/2006 | Miller |
| 2006/0241515 A1 | 10/2006 | Jones et al. |
| 2006/0258953 A1* | 11/2006 | Lee .................. A61B 10/0275 600/562 |
| 2006/0258956 A1 | 11/2006 | Haberstich et al. |
| 2007/0016101 A1 | 1/2007 | Feldman et al. |
| 2007/0027407 A1 | 2/2007 | Miller |
| 2007/0032741 A1 | 2/2007 | Hibner et al. |
| 2007/0073326 A1 | 3/2007 | Miller et al. |
| 2007/0090788 A1 | 4/2007 | Hansford et al. |
| 2007/0106176 A1 | 5/2007 | Mark et al. |
| 2007/0118049 A1 | 5/2007 | Viola |
| 2007/0149894 A1 | 6/2007 | Heske et al. |
| 2007/0161925 A1 | 7/2007 | Quick et al. |
| 2007/0167782 A1 | 7/2007 | Callahan et al. |
| 2007/0179401 A1 | 8/2007 | Hibner |
| 2007/0213590 A1 | 9/2007 | Squicciarina |
| 2007/0213630 A1 | 9/2007 | Beckman et al. |
| 2007/0213632 A1 | 9/2007 | Okazaki et al. |
| 2007/0219572 A1 | 9/2007 | Deck et al. |
| 2007/0236180 A1 | 10/2007 | Rodgers |
| 2007/0239067 A1 | 10/2007 | Hibner et al. |
| 2007/0255173 A1 | 11/2007 | Hibner |
| 2007/0270710 A1 | 11/2007 | Frass et al. |
| 2007/0276288 A1 | 11/2007 | Khaw |
| 2007/0287933 A1 | 12/2007 | Phan et al. |
| 2007/0293788 A1 | 12/2007 | Entrekin et al. |
| 2008/0004545 A1 | 1/2008 | Garrison |
| 2008/0007217 A1 | 1/2008 | Riley |
| 2008/0015429 A1 | 1/2008 | Tsonton et al. |
| 2008/0021487 A1 | 1/2008 | Heisler |
| 2008/0021488 A1 | 1/2008 | Berberich |
| 2008/0030170 A1 | 2/2008 | Dacquay et al. |
| 2008/0064925 A1 | 3/2008 | Gill et al. |
| 2008/0064984 A1 | 3/2008 | Pflueger |
| 2008/0071193 A1 | 3/2008 | Reuber et al. |
| 2008/0079391 A1 | 4/2008 | Schroeck et al. |
| 2008/0110261 A1 | 5/2008 | Randall et al. |
| 2008/0135443 A1 | 6/2008 | Frojd et al. |
| 2008/0146962 A1 | 6/2008 | Ritchie et al. |
| 2008/0146965 A1 | 6/2008 | Privitera et al. |
| 2008/0154151 A1 | 6/2008 | Ritchart et al. |
| 2008/0161682 A1 | 7/2008 | Kendrick et al. |
| 2008/0161718 A1 | 7/2008 | Schwindt |
| 2008/0161719 A1 | 7/2008 | Miller et al. |
| 2008/0161720 A1 | 7/2008 | Nicoson |
| 2008/0183099 A1 | 7/2008 | Jorgensen et al. |
| 2008/0195066 A1 | 8/2008 | Speeg et al. |
| 2008/0200833 A1 | 8/2008 | Hardin et al. |
| 2008/0200836 A1 | 8/2008 | Speeg et al. |
| 2008/0208194 A1 | 8/2008 | Bichenbach |
| 2008/0215056 A1 | 9/2008 | Miller et al. |
| 2008/0221443 A1 | 9/2008 | Ritchie et al. |
| 2008/0221444 A1 | 9/2008 | Ritchie et al. |
| 2008/0221478 A1 | 9/2008 | Ritchie et al. |
| 2008/0221479 A1 | 9/2008 | Ritchie et al. |
| 2008/0221480 A1 | 9/2008 | Hibner et al. |
| 2008/0223904 A1 | 9/2008 | Marczyk |
| 2008/0228104 A1 | 9/2008 | Uber et al. |
| 2008/0232604 A1 | 9/2008 | Dufresne et al. |
| 2008/0234715 A1 | 9/2008 | Pescue et al. |
| 2008/0281225 A1 | 11/2008 | Spero et al. |
| 2008/0287826 A1 | 11/2008 | Videbaek et al. |
| 2008/0306404 A1 | 12/2008 | Ronald |
| 2008/0306406 A1 | 12/2008 | Thompson et al. |
| 2008/0308607 A1 | 12/2008 | Timm et al. |
| 2008/0312554 A1* | 12/2008 | Garrison .......... A61B 10/0275 600/566 |
| 2008/0319341 A1 | 12/2008 | Taylor et al. |
| 2009/0030405 A1 | 1/2009 | Quick et al. |
| 2009/0062624 A1 | 3/2009 | Neville |
| 2009/0088666 A1 | 4/2009 | Miller et al. |
| 2009/0125062 A1 | 5/2009 | Arnin |
| 2009/0137927 A1 | 5/2009 | Miller |
| 2009/0171243 A1 | 7/2009 | Hibner et al. |
| 2009/0204021 A1 | 8/2009 | Shabaz et al. |
| 2009/0082695 A1 | 9/2009 | Whitehead |
| 2009/0227893 A1 | 9/2009 | Coonahan et al. |
| 2010/0030020 A1 | 2/2010 | Sanders et al. |
| 2010/0063416 A1 | 3/2010 | Cicenas et al. |
| 2010/0152611 A1 | 6/2010 | Parihar et al. |
| 2010/0160820 A1 | 6/2010 | Weikel, Jr. et al. |
| 2010/0210966 A1 | 8/2010 | Videbaek |
| 2010/0234760 A1* | 9/2010 | Almazan .......... A61B 10/0275 600/566 |
| 2010/0292607 A1 | 11/2010 | Moore et al. |
| 2010/0312140 A1 | 12/2010 | Smith et al. |
| 2010/0317995 A1 | 12/2010 | Hibner et al. |
| 2010/0317997 A1 | 12/2010 | Hibner et al. |
| 2010/0317998 A1 | 12/2010 | Hibner et al. |
| 2011/0071391 A1* | 3/2011 | Speeg .................. A61B 90/39 600/431 |
| 2011/0152715 A1 | 6/2011 | Delap et al. |
| 2011/0160611 A1 | 6/2011 | Ritchart et al. |
| 2011/0224577 A1 | 9/2011 | Park |
| 2011/0313316 A1 | 12/2011 | Ranpura et al. |
| 2012/0116248 A1* | 5/2012 | McWeeney ........ A61B 10/0283 600/567 |
| 2012/0130274 A1 | 5/2012 | Persat |
| 2012/0197157 A1* | 8/2012 | Ryan .................. A61B 10/0266 600/567 |
| 2012/0253228 A1 | 10/2012 | Schembre et al. |
| 2014/0100448 A1 | 4/2014 | Neilan |
| 2014/0207021 A1 | 7/2014 | Snow |
| 2014/0276205 A1 | 9/2014 | Miller et al. |
| 2016/0030016 A1* | 2/2016 | McWeeney ........ A61B 10/0275 600/567 |
| 2016/0081678 A1 | 3/2016 | Kappel et al. |
| 2018/0333145 A1 | 11/2018 | Snow |
| 2018/0333147 A1 | 11/2018 | Snow et al. |
| 2021/0093305 A1 | 4/2021 | Peliks et al. |

FOREIGN PATENT DOCUMENTS

| | | |
|---|---|---|
| DE | 4120329 | 1/1992 |
| DE | 4041614 | 10/1992 |
| DE | 2453058 | 5/1996 |
| DE | 10034297 | 4/2001 |
| DE | 10026303 | 2/2002 |
| DE | 20209525 | 11/2002 |
| DE | 10235480 | 2/2004 |
| EP | 0433717 | 6/1991 |
| EP | 541377 | 5/1993 |
| EP | 0890339 | 1/1999 |
| EP | 0995400 | 4/2000 |
| EP | 1074271 | 2/2001 |
| EP | 1520518 | 4/2005 |
| EP | 1579809 | 9/2005 |
| EP | 1665958 | 6/2006 |
| EP | 2095772 | 2/2009 |
| EP | 2106750 | 10/2009 |
| FR | 1345429 | 12/1963 |
| FR | 2739293 | 4/1997 |
| GB | 2018601 | 10/1979 |
| GB | 2038640 | 12/1979 |
| JP | H10508504 | 8/1998 |
| JP | 2005530554 | 10/2005 |
| JP | 2006509545 | 3/2006 |
| JP | 2006528907 | 12/2006 |
| JP | 2007502159 | 2/2007 |
| RU | 1454457 | 1/1989 |
| WO | 199314700 | 8/1993 |
| WO | 199416181 | 7/1994 |
| WO | 199428801 | 12/1994 |
| WO | 199628097 | 9/1996 |
| WO | 199825522 | 6/1998 |
| WO | 199831285 | 7/1998 |

(56) References Cited

FOREIGN PATENT DOCUMENTS

| WO | 199835615 | 8/1998 |
| WO | 199846290 | 10/1998 |
| WO | 199933501 | 7/1999 |
| WO | 200004832 | 2/2000 |
| WO | 200030546 | 6/2000 |
| WO | 200059378 | 10/2000 |
| WO | 200172230 | 10/2001 |
| WO | 200222023 | 3/2002 |
| WO | 200232318 | 4/2002 |
| WO | 2002069808 | 9/2002 |
| WO | 20040757719 | 9/2004 |
| WO | 2005013830 | 2/2005 |
| WO | 2006015302 | 2/2006 |
| WO | 2007047128 | 4/2007 |
| WO | 2007095330 | 8/2007 |
| WO | 2007112751 | 10/2007 |
| WO | 2008021687 | 2/2008 |
| WO | 2008024684 | 2/2008 |
| WO | 200804812 | 4/2008 |
| WO | 2008131362 | 10/2008 |
| WO | 2010107424 | 9/2010 |

OTHER PUBLICATIONS

International Search Report and Written Opinion dated Sep. 4, 2018 for PCT/US2018/033188.
Office Action dated Jul. 1, 2020 for U.S. Appl. No. 15/980,116.
Office Action dated May 12, 2020 for U.S. Appl. No. 15/982,777.
European Search Report dated Feb. 1, 2021 for EP18802126.5.
Office Action dated Nov. 27, 2020 for U.S. Appl. No. 15/982,777.
Office Action dated Mar. 24, 2021 for U.S. Appl. No. 15/980,116.

* cited by examiner

ROTATING BIOPSY NEEDLE

RELATED APPLICATIONS

This application claims priority to U.S. Provisional Application No. 62/508,882, filed on May 19, 2017 and titled, "Rotating Biopsy Needle," which is hereby incorporated by reference in its entirety.

TECHNICAL FIELD

The present disclosure relates generally to medical devices. More specifically, the present disclosure relates to biopsy needle assemblies configured for use with tissue biopsy devices, including needle assemblies configured to decrease, minimize, or eliminate axial translation impact at a tissue sample collection site.

BRIEF DESCRIPTION OF THE DRAWINGS

The embodiments disclosed herein will become more fully apparent from the following description and appended claims, taken in conjunction with the accompanying drawings. The drawings depict only typical embodiments, which embodiments will be described with additional specificity and detail in connection with the drawings in which:

FIG. 2A is a detail view of the needle of FIG. 2 taken through detail section 2A.

FIG. 2B is a perspective cross-section view of the distal end portion of the needle of FIG. 2A taken through plane 2B.

DETAILED DESCRIPTION

Figure 1:
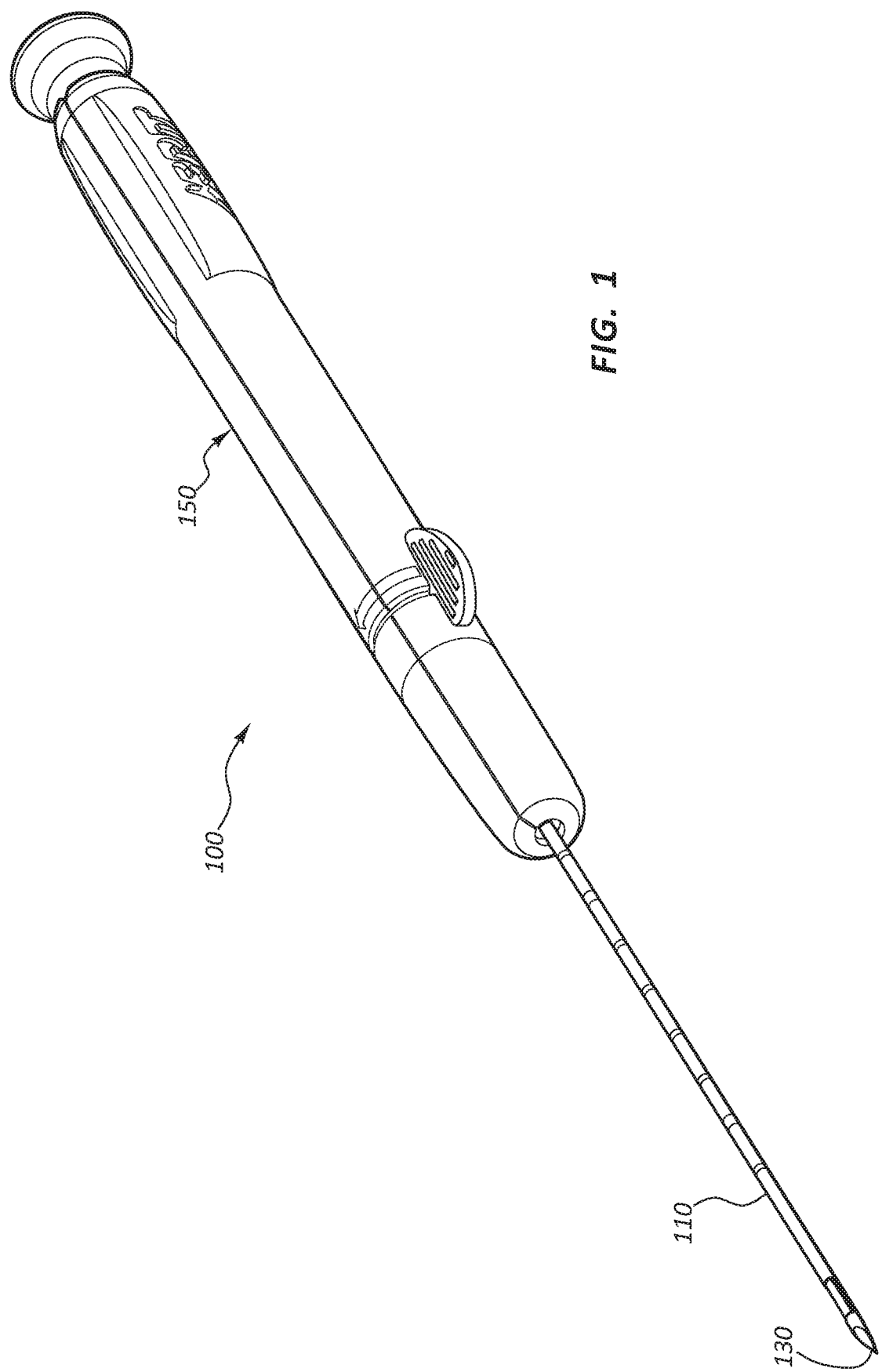
FIG. 1 is a perspective view of a biopsy needle assembly.

Tissue biopsy devices may be configured to retrieve tissue samples from various locations within a patient's body. For example, a biopsy device may comprise a biopsy needle assembly, or needle assembly, including tubular members, cutting styli, styli, cannula, and/or other components configured to access and sever a tissue sample in a medical procedure commonly referred to as Core Needle Biopsy. The needle assembly may be inserted into a location within the body through the skin of the patient (percutaneous access), through an open incision or may be advanced through a body lumen or other structure. Furthermore, a biopsy device may comprise a handle or actuator configured to axially displace or rotate at least a portion of the needle assembly such that the needle assembly severs the targeted tissue sample.

Medical devices and related components, as described in greater detail below, may be configured to facilitate a Core Needle Biopsy procedure. In some circumstances, the medical devices are designed to facilitate tissue biopsy utilizing a non-axial displacement technique.

Embodiments may be understood by reference to the drawings, wherein like parts are designated by like numerals throughout. It will be readily understood by one of ordinary skill in the art having the benefit of this disclosure that the components of the embodiments, as generally described and illustrated in the figures herein, could be arranged and designed in a wide variety of different configurations. Thus, the following more detailed description of various embodiments, as represented in the figures, is not intended to limit the scope of the disclosure, but is merely representative of various embodiments. While the various aspects of the embodiments are presented in drawings, the drawings are not necessarily drawn to scale unless specifically indicated.

It will be appreciated that various features are sometimes grouped together in a single embodiment, figure, or description thereof for the purpose of streamlining the disclosure. Many of these features may be used alone and/or in combination with one another.

The phrases "coupled to" and "in communication with" refer to any form of interaction between two or more entities, including mechanical, electrical, magnetic, electromagnetic, fluid, and thermal interaction. Two components may be coupled to or in communication with each other even though they are not in direct contact with each other. For example, two components may be coupled to or in communication with each other through an intermediate component.

The directional terms "distal" and "proximal" are given their ordinary meaning in the art. That is, the distal end of a medical device means the end of the device furthest from the practitioner during use. The proximal end refers to the opposite end, or the end nearest the practitioner during use. As specifically applied to the syringe portion of an inflation device, the proximal end of the syringe refers to the end nearest the handle and the distal end refers to the opposite end, the end nearest the inlet/outlet port of the syringe. Thus, if at one or more points in a procedure a physician changes the orientation of a syringe, as used herein, the term "proximal end" always refers to the handle end of the syringe (even if the distal end is temporarily closer to the physician).

"Tissue" is used in its broadest sense, to refer to any tissue or substance within the human body.

FIGS. 1-8C illustrate different views the biopsy needle device 100 and related components. In certain views each device may be coupled to, or shown with, additional components not included in every view. Further, in some views only selected components are illustrated, to provide detail into the relationship of the components. Some components may be shown in multiple views, but not discussed in connection with every view. Disclosure provided in connection with any figure is relevant and applicable to disclosure provided in connection with any other figure or embodiment.

FIG. 1 is a perspective view of a biopsy needle device 100. As illustrated, the device 100 may comprise an outer tubular member or needle 110, an inner elongate member or stylet 130 disposed within the needle and an actuator or handle 150 operably coupled to the proximal portions of the needle 110 and stylet 130.

Figure 2:
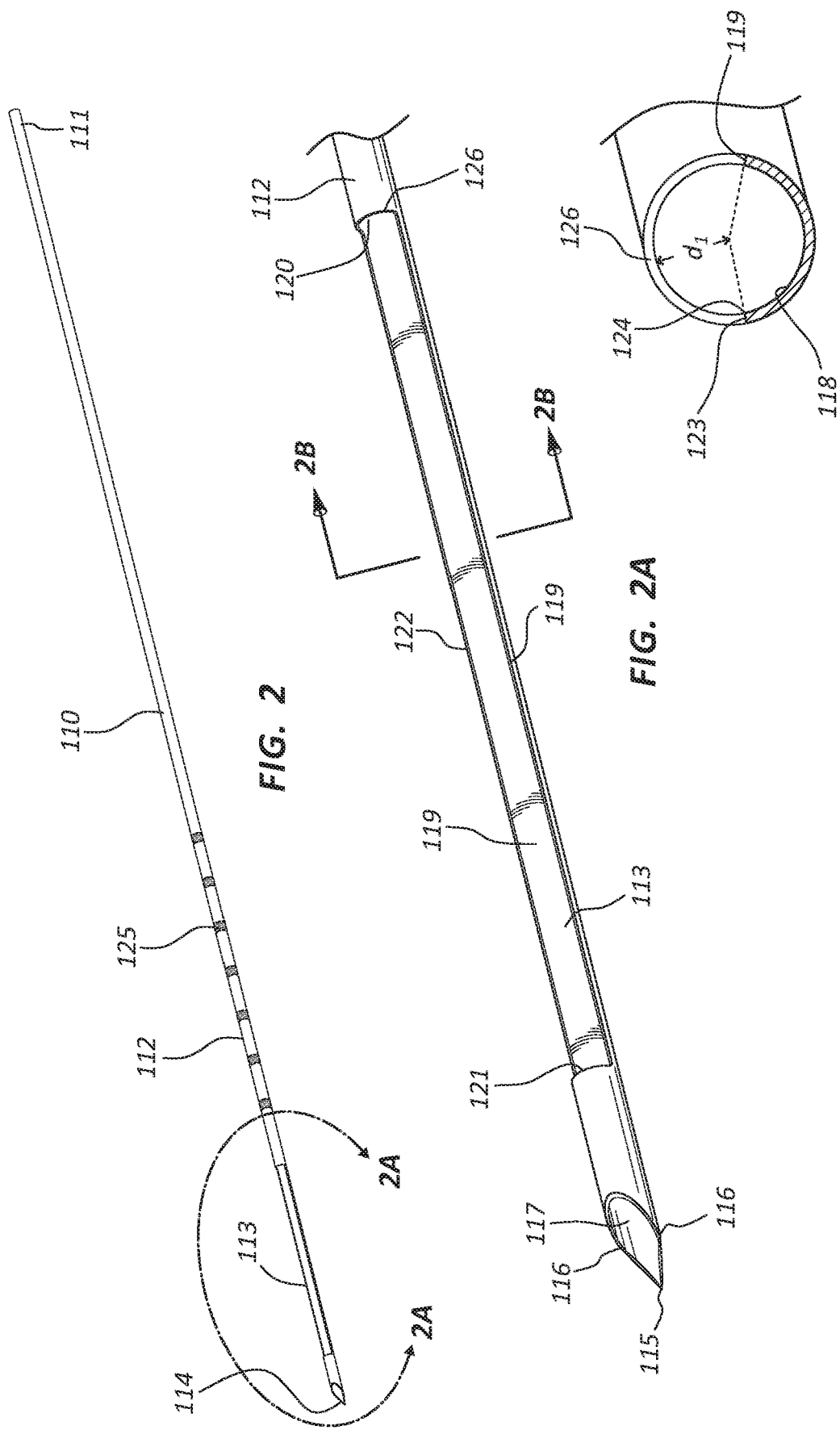
FIG. 2 is a perspective view of a needle of the biopsy needle assembly of FIG. 1.

FIG. 2 is a perspective view of the needle 110 of FIG. 1, FIG. 2A is a detail view of the distal end portion 112 of the needle 110 of FIG. 2 and FIG. 2B is a perspective cross-section view of the distal end portion of the needle of FIG. 2A taken through plane 2B. The needle 110 may comprise a distal end portion 112, proximal end portion 111 and a lumen 117. The needle 110 may range in diameter from 9 gauge to 22 gauge, including, from 14 gauge to 20 gauge, and from 14 ga to 17 ga. The length of the needle 110 may range from 2 cm to 20 cm, including, from 6 cm to 10 cm, from 2 cm to 16 cm, and from 4 cm to 12 cm. The lumen 117 may be sized to accommodate the stylet (130 of FIG. 3) such that the stylet 130 may be disposed within the lumen 117 and may rotate within the lumen 117 around a longitudinal axis. The needle 110 may be manufactured from a medical grade stainless steel material and formed with a thin wall 118.

In some embodiments the proximal end portion 111 of the needle 110 may be configured to be fixedly coupled to the actuator 150 through any suitable technique, including, boding, welding, insert molding, etc. Alternatively, the proximal end portion 111 of the needle 110 may be configured to be releasably coupled to the actuator 150. In some procedures, the needle 110 may be utilized as an introducer to facilitate removal of multiple samples from a single insertion of needle 110. For example, the needle 110 and stylet 130 may be inserted through a patient's skin and into the target tissue or lesion. An initial tissue sample may be taken and the stylet 130 may be removed from the proximal end portion 111 of the needle 110 and the tissue sample removed. Subsequently, the same stylet 130 (or a second stylet) may be inserted into the proximal end portion 111 of the needle 110 for a second tissue sample. This technique may be repeated until the practitioner has obtained the desired quantity and number of tissue samples.

In some embodiments the distal end portion 112 of the needle 110 may be configured facilitate penetration of the needle 110 to into body tissue. The distal end portion 112 of needle 110 may comprise a tissue penetration point 114. The penetration point 114 may comprise a sharp tip 115 and at least one facet 116. In some embodiments it comprises at least two facets 116 located on opposite sides of the penetration point 114 such that the penetration point 114 is configured to penetrate through tissue, including skin and/or a portion of the target tissue or lesion, without coring tissue restricting or preventing passage of tissue into the distal end of the lumen 117. Other embodiments of the penetration point 114 may be configured as needle tip configurations, such as, but not limited to, a pencil point, Greene point, Quincke, Hustead, or Toughy.

In certain embodiments, the distal end portion 112 of the needle 110 may comprise a cutout or window 113. The window 113 may extend along the longitudinal axis of the needle. The window may be generally rectangular in shape comprising longitudinal edges 119 and transverse edges 120. The depth $d_1$ of the window 113 from the needle 110 outer surface to the longitudinal edge 119 may be approximately 50% of the needle 110 diameter. The longitudinal edge 119 may be generally parallel to the longitudinal axis of the needle 110. In some embodiments, the longitudinal edge 119 may be angled in an opposite direction from the angle of the stylet cutting blade 135. The angle may range from 1 degree to 5 degrees. A distal transverse edge 121 of the window 113 may be located approximately 0.5 cm to 1 cm from the penetration point 114 of the needle 110. The window 113 may have a length of at least 0.5 cm to at least 3 cm, including 1 cm to 2.5 cm. The window 113 may be formed by any suitable technique such as grinding, electrical discharge machining, chemical etching, etc.

In some embodiments, at least one longitudinal edge 119 of the window 113 may comprise a knife edge 122. The knife edge 122 may include a bevel 123 configured with a sharp edge 124. The angle of the bevel 123 may range from approximately 0 degrees to approximately 15 degrees from a horizontal plane lying across the longitudinal edges 119. The sharp edge 124 may be disposed on the inside of the wall 118 of needle. The bevel 123 may be formed by suitable manufacturing techniques known in the art such as, grinding, electrical discharge, chemical etching, etc. The knife edge 122 may be configured to cooperate with the cutting blade (135 of FIG. 3) in a manner analogous to the operation of scissor blades to cut or sever a tissue sample from surrounding tissue utilizing a shear force. This interaction is discussed in more detail in connection with FIGS. 6A-6C. For example, tissue may be caught between the knife edge 122 and the cutting blade 132 such that a sheering force may cut or sever the tissue.

In certain embodiments the needle 110 may comprise a plurality of indicia 125 configured to indicate to the practitioner a distance that the needle 110 has advanced into a body tissue (for clarity not all indicia 125 are labeled). For example, each indicium 125 may be positioned 1 cm apart; thus, if the practitioner displaces the needle 110 into a body tissue up to the third indicia 125 from the distal end portion 112 of the needle 110, it may indicate to the practitioner that approximately 3 cm of the needle 110 has been displaced into the body tissue. In some embodiments, the indicia 125 may comprise a plurality of substantially evenly spaced annular lines, marks, or grooves on an outside surface of the needle 110. In certain embodiments, the indicia 125 may comprise a plurality of tick marks or the indicia may not be evenly spaced.

In certain embodiments, a portion or portions of at least one of the components of the biopsy needle device 100, including, but not limited to, the needle penetration point 114, the indicia 125, and/or the stylet 130, may comprise a radiopaque material and/or an echogenic material. A radiopaque material (for example, in combination with a fluoroscope) may aid the practitioner in directing or displacing the needle assembly to a desired or predetermined position within the body tissue of the patient. Bismuth, gold, or other radiopaque materials alone, or in combination, may be used. An echogenic material or surface (for example, in combination with ultrasound) may analogously aid the practitioner in directing or displacing the needle assembly to a desired or predetermined position within the body tissue of the patient. Surface disruptions such as texturing, grooves, dimples, or a combination of materials may also be used.

Figure 3:
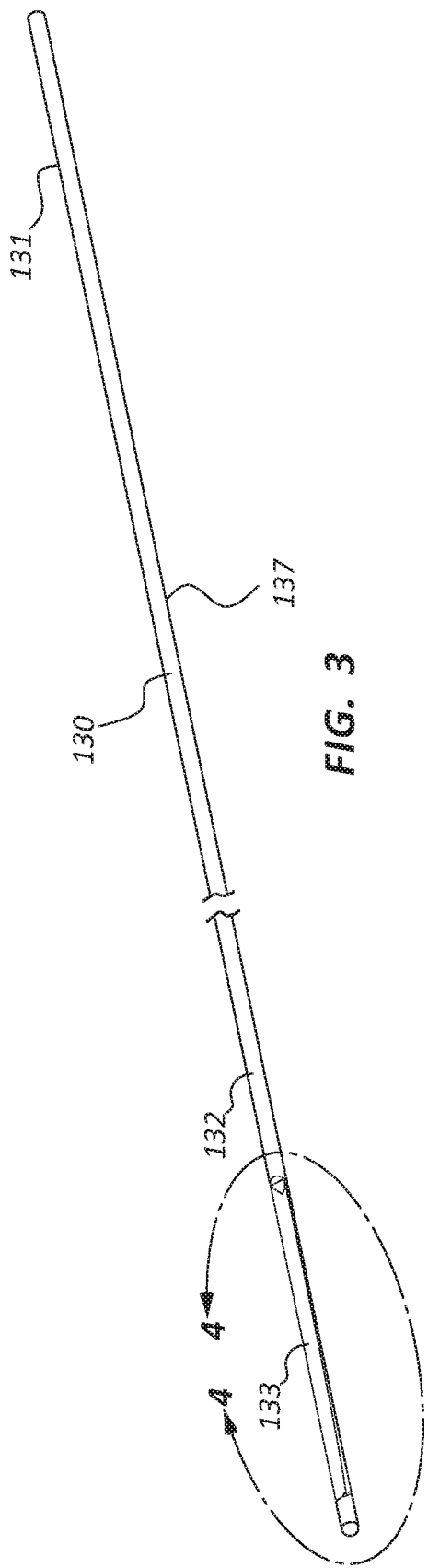
FIG. 3 is a perspective view of a stylet of the biopsy needle assembly of FIG. 1.
Figure 4:
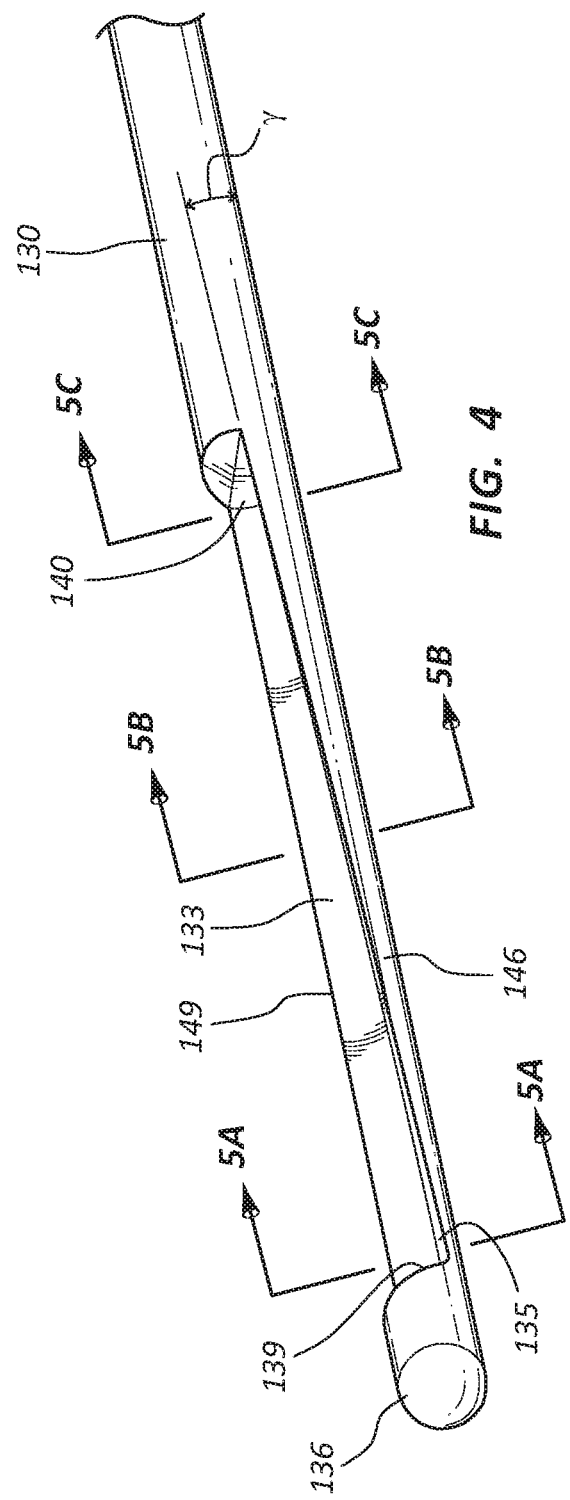
FIG. 4 is a detail view of the stylet of FIG. 3 taken through detail section 4.
Figure 5A:
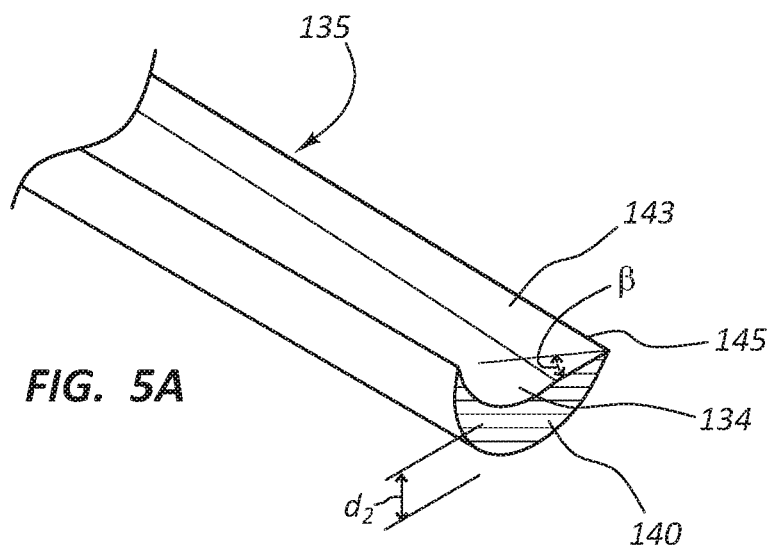
FIG. 5A is a perspective cross-section view of a portion of the stylet of FIG. 4 taken through plane 5A.
Figure 5B:
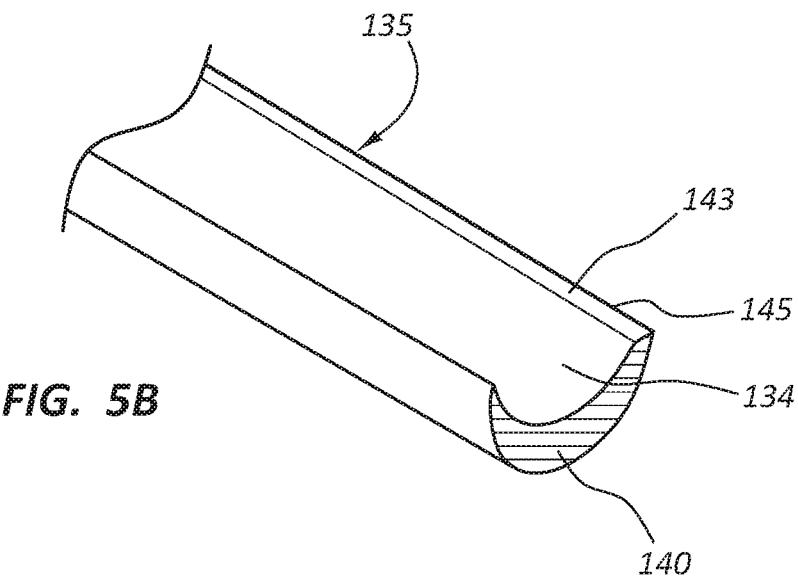
FIG. 5B is a perspective cross-section view of the stylet of FIG. 4 taken through plane 5B.
Figure 5C:
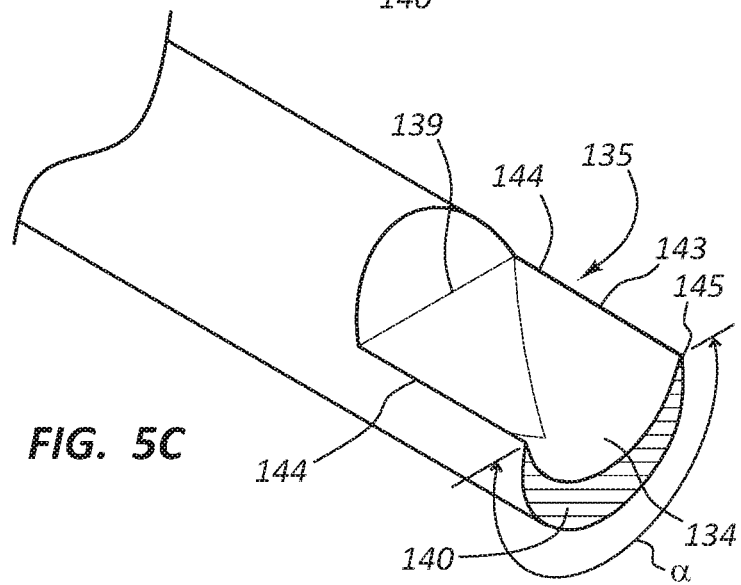
FIG. 5C is a perspective cross-section view the stylet of FIG. 4 taken through plane 5C.
Figure 6A:
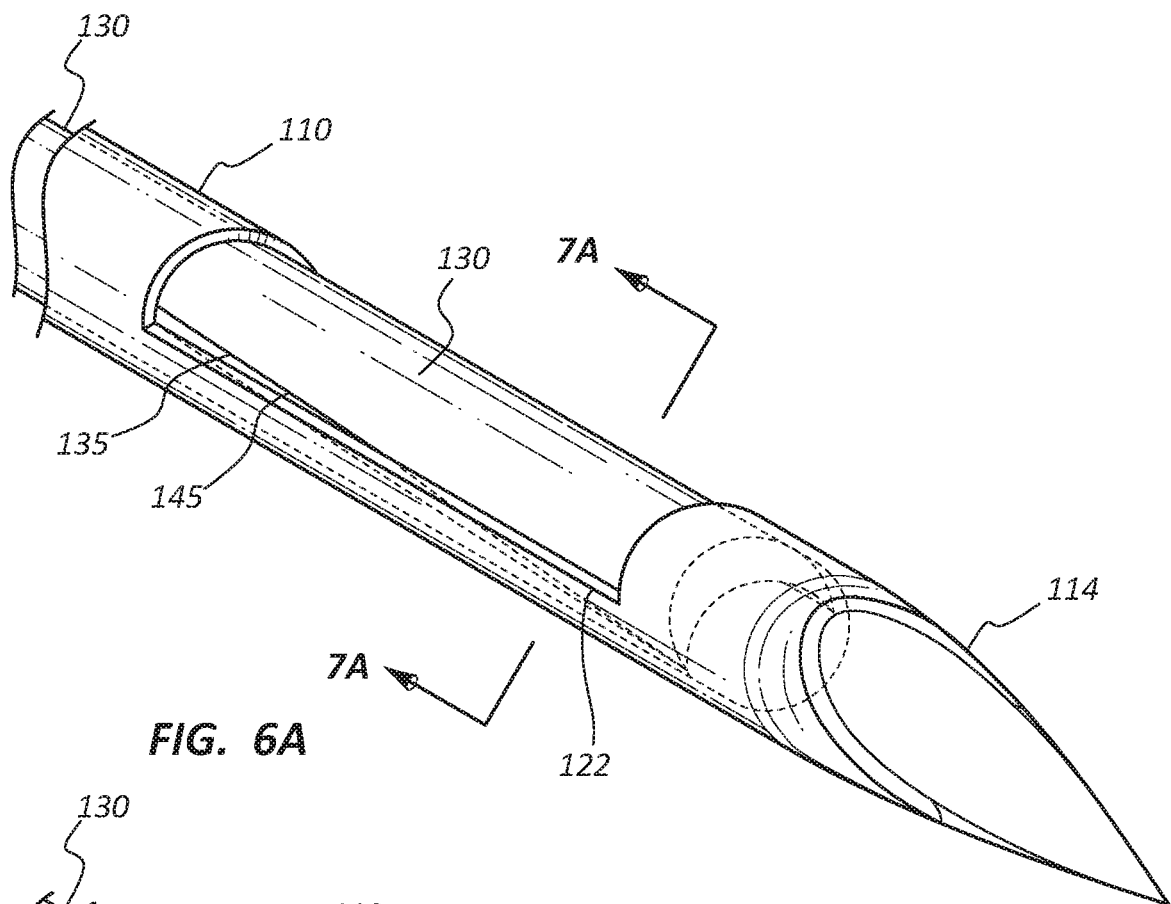
FIG. 6A is a perspective view of the distal end portion of the biopsy needle assembly of FIG. 1 in a first configuration.
Figure 6B:
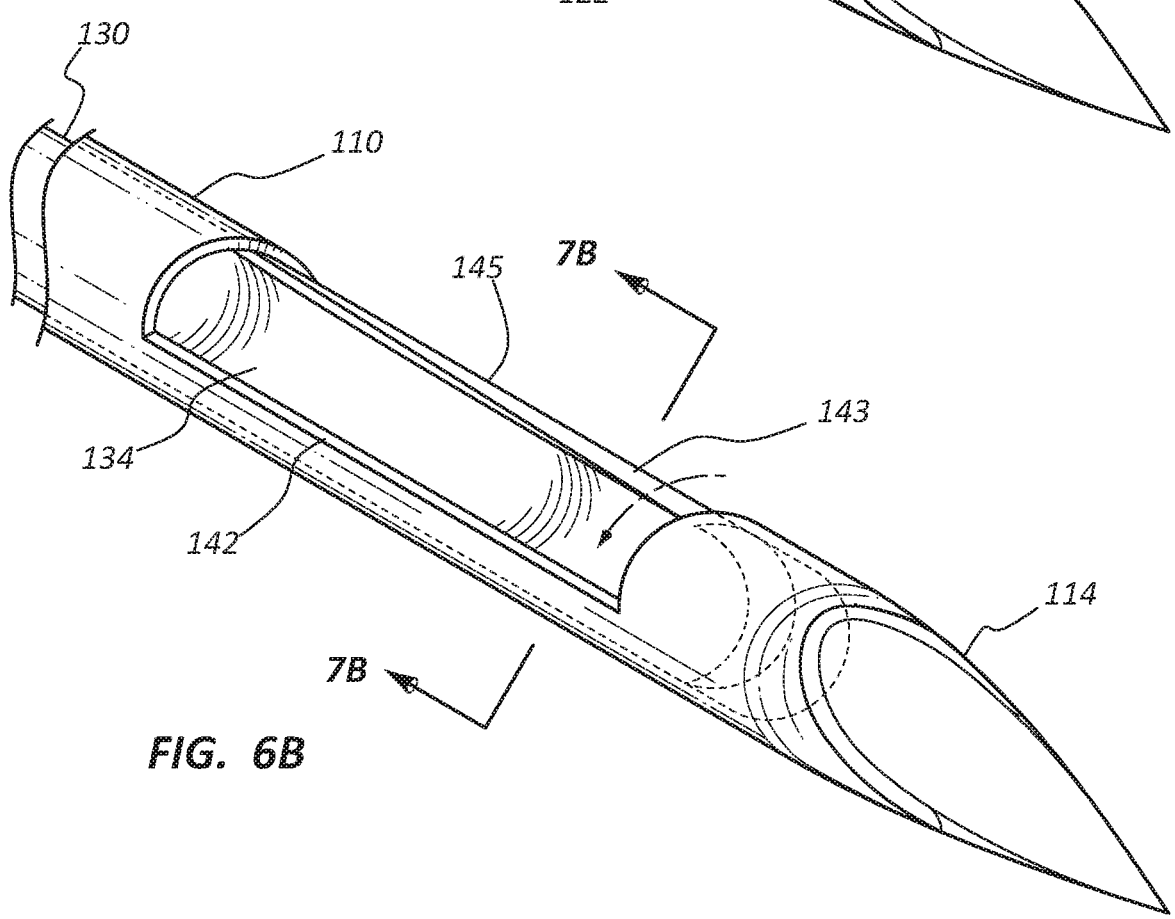
FIG. 6B is a perspective view of the distal end portion of the biopsy needle assembly of FIG. 1 in a second configuration.
Figure 7A:
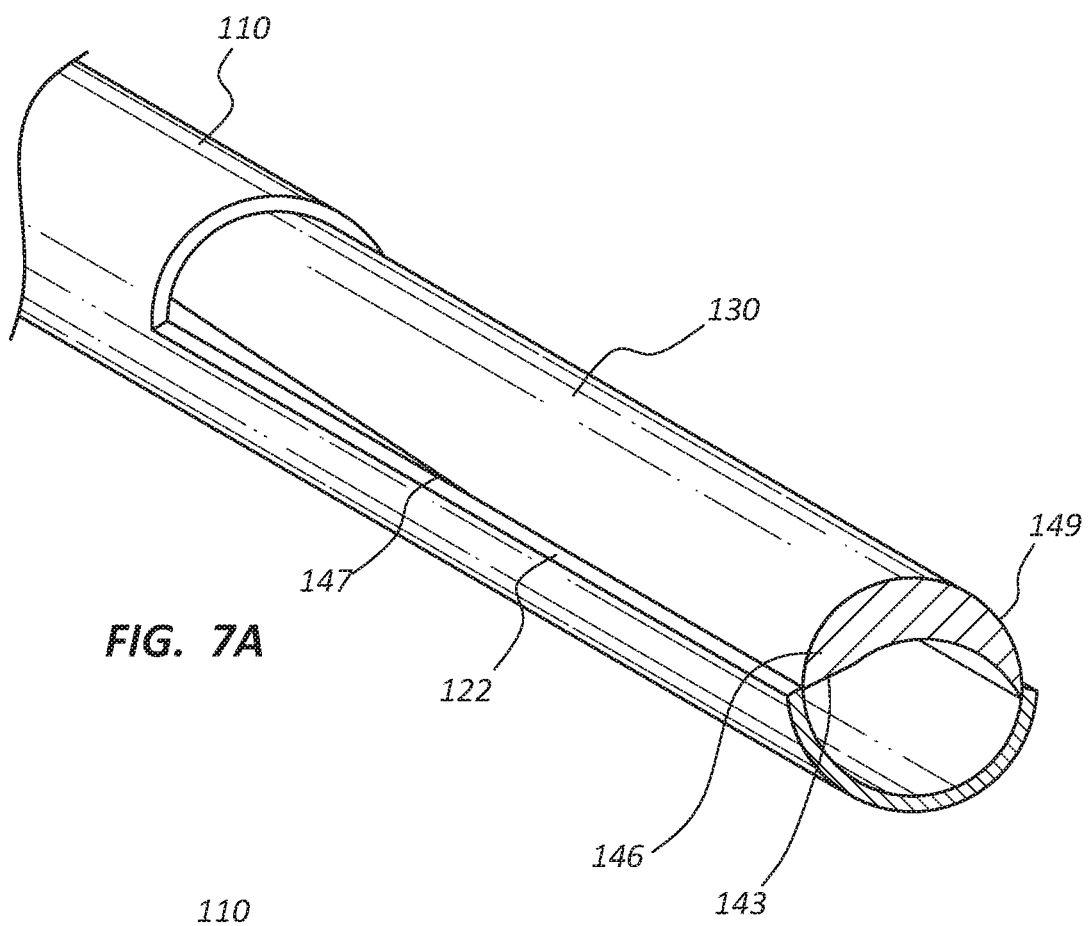
FIG. 7A is a perspective cross-section view of the needle and the stylet of FIG. 6A through line 7A, with the needle and stylet in the configuration of 6A.
Figure 7B:
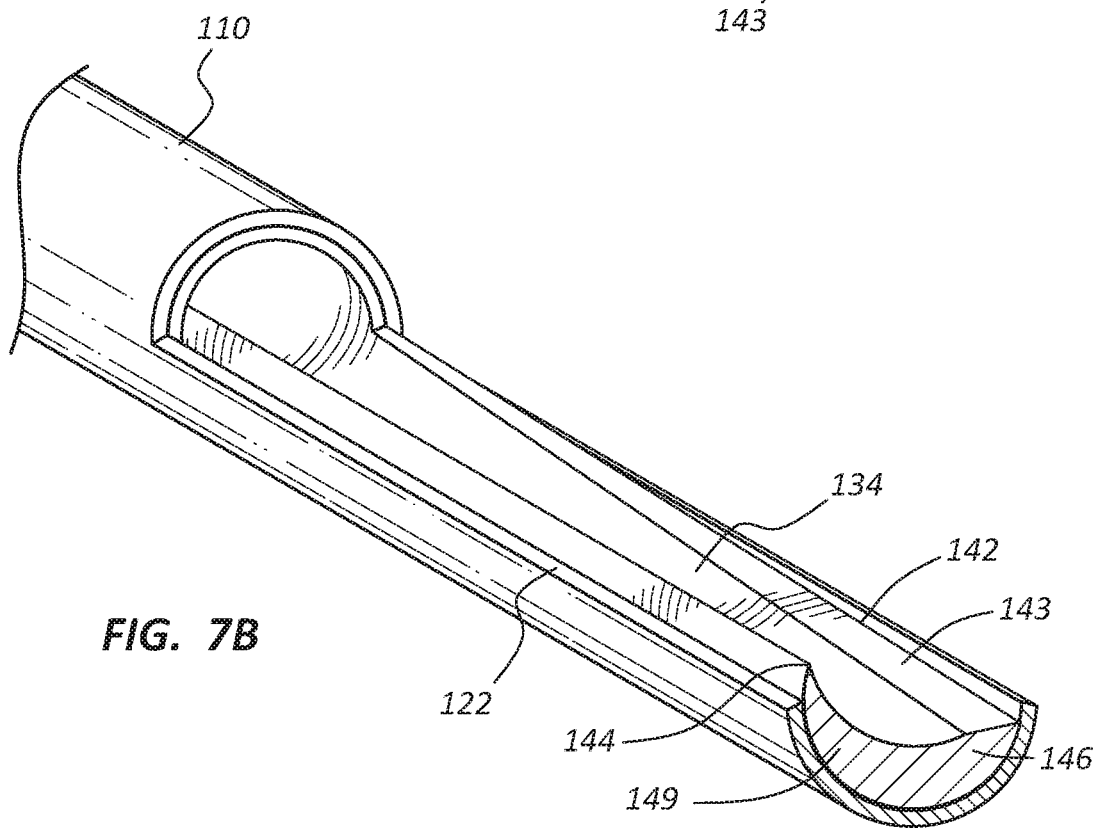
FIG. 7B is a perspective cross-section view of the needle and the stylet of FIG. 6B through plane 7B, with the needle and stylet in the configuration of 6B.

FIGS. 3-5C are views of the stylet 130 of FIG. 1. FIG. 3 is a perspective view of the stylet 130. FIG. 4 is a detail view of the distal end portion 132 of the stylet 130 of FIG. 3 taken through detail view 4. FIGS. 5A-5C are perspective section views of the stylet notch 133 of FIG. 4 at planes 5A, 5B and 5C, respectively. The stylet 130 may comprise a distal end portion 132 including a distal end 136, a proximal end portion 131, and a shaft 137. In some embodiments, the distal end 136 may be blunted. For example, the distal end 136 may have a bullnose shape or be squared off. Alternatively, the distal end 136 may be beveled such that the bevel angle matches the angle of the penetration point 114 of the needle 110. The distal end 136 may be configured to occlude the distal end of needle lumen 117 such that tissue is restricted or prevented from entering the distal end of lumen 117. The proximal end portion 132 may be configured to couple with the actuator 150 such that the actuator may rotate the stylet 130 180 degrees in one direction to open the needle window 113 and allow for a tissue sample to collapse or prolapse through the window 113, further rotation the stylet 130 180 degrees in the opposite direction may cut or sever the tissue sample from surrounding tissue. The stylet 130 may be of unitary construction. The stylet 130 may be formed from a rod and made from a material such as stainless steel. In certain embodiments the stylet 130 may be disposed within the lumen 117 of needle 110 and be configured to rotate within the lumen 117, to provide flexural strength to the needle 110, and to cooperate with the needle window 113 to sever and capture a target tissue sample. The distal end 136 of the stylet 130 may be disposed adjacent the needle penetrating point 114 and may or may not extend beyond the needle penetrating point 114.

In some embodiments, the stylet distal end portion 131 may further comprise a cutout or notch 133. The notch 133 may be generally rectangular in shape with a longitudinal side 138 of the notch 133 extending along the longitudinal axis of the stylet 130. In some embodiments, the length of the notch 133 may be longer than the needle window 113 such that a distal end 139 of the notch 133 may be positioned distally of the distal transverse edge 121 of the window 113 and a proximal end 140 of the notch 133 may be positioned proximally of a proximal transverse edge 126 of the window 113 when the stylet 130 is disposed within the needle lumen 117.

In certain embodiments, the notch 133 may comprise a trough 134 configured to retain the cut or severed tissue sample. A transverse section of the trough 134 may be crescent shaped having a convex edge 127, a concave edge 128, and two tips 144 near the proximal end 140 of the notch 133 and form approximately 65% of a circle (γ of FIG. 5C). A side 148 of the crescent shaped trough 134 may be progressively truncated moving from the notch proximal end 140 to the notch distal end 139 such that the side 146 of the trough 134 may be shorter near the distal end 139 of the notch 133 than near the proximal end 140 of the notch 133. A second side 149 of the trough 134 may be configured with a constant height from the distal end 139 to the proximal end 140. The thickest portion of the trough wall 141 may be located at the bottom of the trough 134 and may be approximately 25% ($d_2$ of FIG. 5A) of the diameter of the stylet 130.

In some embodiments, the notch 133 may comprise a cutting blade 135. The cutting blade 135 may comprise a bevel 143 and a cutting edge 142. The bevel 143 may have an angle β of from 25 degrees to 35 degrees, including approximately 30 degrees, from a horizontal plane across the tips 144 of the crescent shaped trough 134 and be angled downwards from the outside surface of the stylet 130 when the trough 134 is oriented upwards. The bevel 143 may progressively widen as the cutoff portion of the trough side 146 increases from the notch proximal end 140 to the notch distal end 139 at about a one to three degree angle. In other words, as the depth of the cutting blade 135 increases within the notch 133 from the proximal end 140 to the distal end 139, more material may be removed from the trough side 146 resulting in a wider bevel near the notch distal end 139 than near the notch proximal end 140.

The outer edge of the bevel 143 may be configured as a squared edge or cutting edge 142. The cutting edge 142 may be sharp. The cutting edge 142 may be curvilinear along the outer diameter of the stylet 130 and may be configured as a helical shape that may incline at approximately one to three degrees (γ of FIG. 4) from the notch distal end 139 to the notch proximal end 140. The helical shaped cutting edge 142 may be configured to make point contact with the knife edge 122 of the window 113 as the stylet 130 may be rotated relative to the needle 110.

Referring to FIGS. 6A-7B, in some embodiments, the knife edge 122 of the needle window 113 may be configured to contact the cutting edge 142 of the cutting blade 135 in a manner analogous to the operation of scissor blades. The inclined orientation of the cutting edge 142 and the level orientation of the knife edge 122 may provide an angel or from 1 degree to 3 degrees and facilitate a point contact 147 between the stylet cutting edge 132 and the knife edge 122 as the stylet cutting edge 132 rotates past the window knife edge 122. The single point contact 147 may facilitate a slicing or lancing of the tissue sample rather than a crushing cut of the tissue sample to sever the sample from the surrounding tissue. The slicing or lancing of the tissue may result in a tissue sample with minimal cell or architectural damage. The minimization of cell or architectural damage may provide a high quality tissue sample for analysis resulting in a more accurate diagnosis for the patient.

In some embodiments, the cutting edge 132 and the knife edge 122 are configured to make simultaneous contact over the full length of the cutting edge 132 and the knife edge 122 resulting in a complete severing of the longitudinal length of the sample tissue at once. For example, the knife edge 122 and the cutting edge 132 may be parallel resulting in an engagement of the full length of the knife edge 122 with the cutting edge 132. In other embodiments, the knife edge 122 may be longitudinally angled or inclined one to three degrees in the opposite direction from the longitudinal angle of the cutting edge 132. The opposing longitudinal angles of the knife edge 122 and the cutting edge 132 may create an increased angle of about 2 degrees to 6 degrees between the knife edge 122 and cutting edge 132. The increased angle of engagement may allow for cutting or severing of the tissue progressively along its longitudinal length. This, in turn, may result in a lower force resulting in less trauma to the tissue.

Figure 8A:
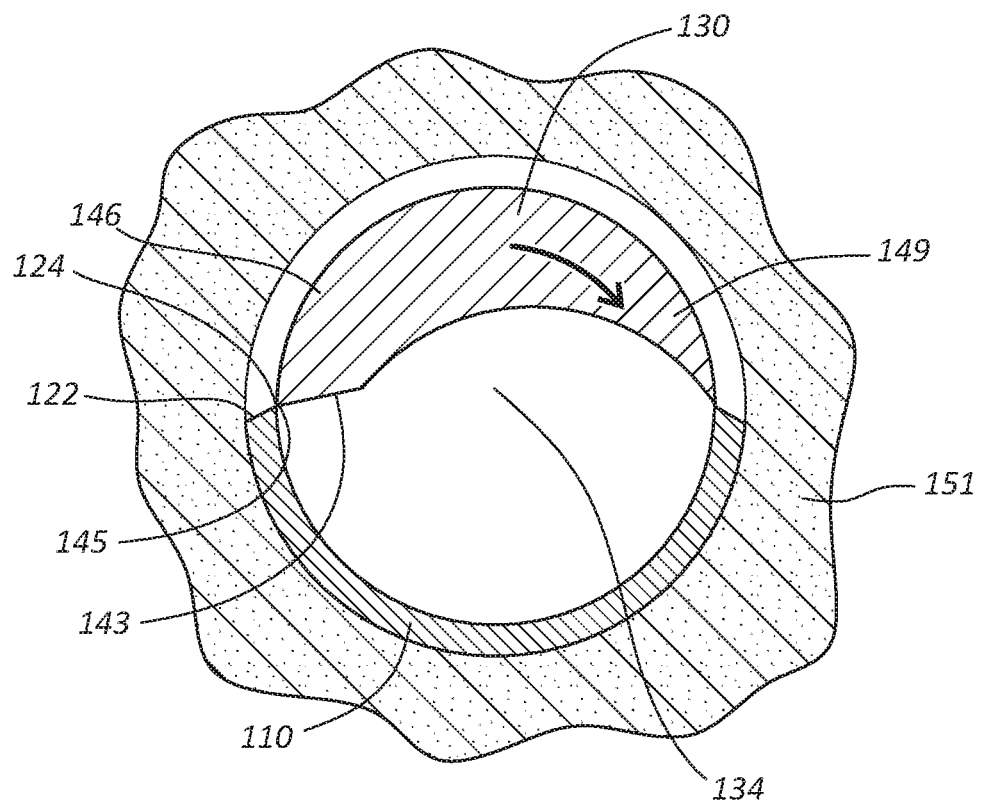
FIG. 8A is a schematic cross-sectional representation of portions of the needle and the stylet of the biopsy needle assembly of FIG. 1 in a first configuration.
Figure 8B:
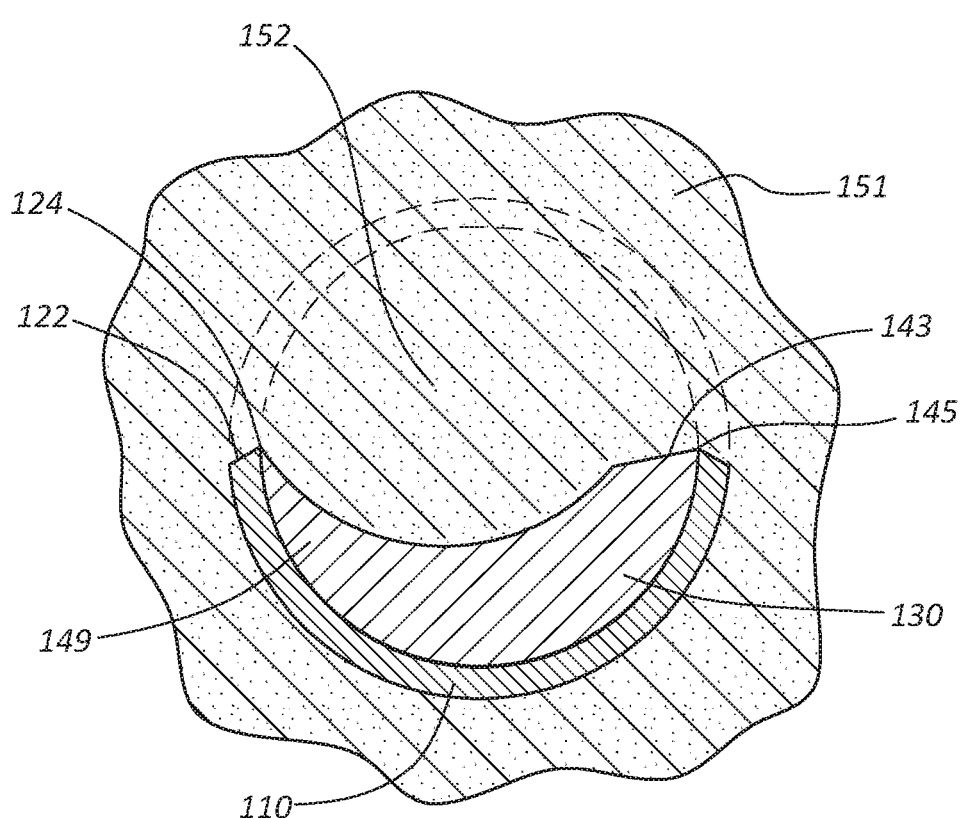
FIG. 8B is a schematic cross-sectional representation of portions of the needle and the stylet of the biopsy needle assembly of FIG. 1 in a second configuration.
Figure 8C:
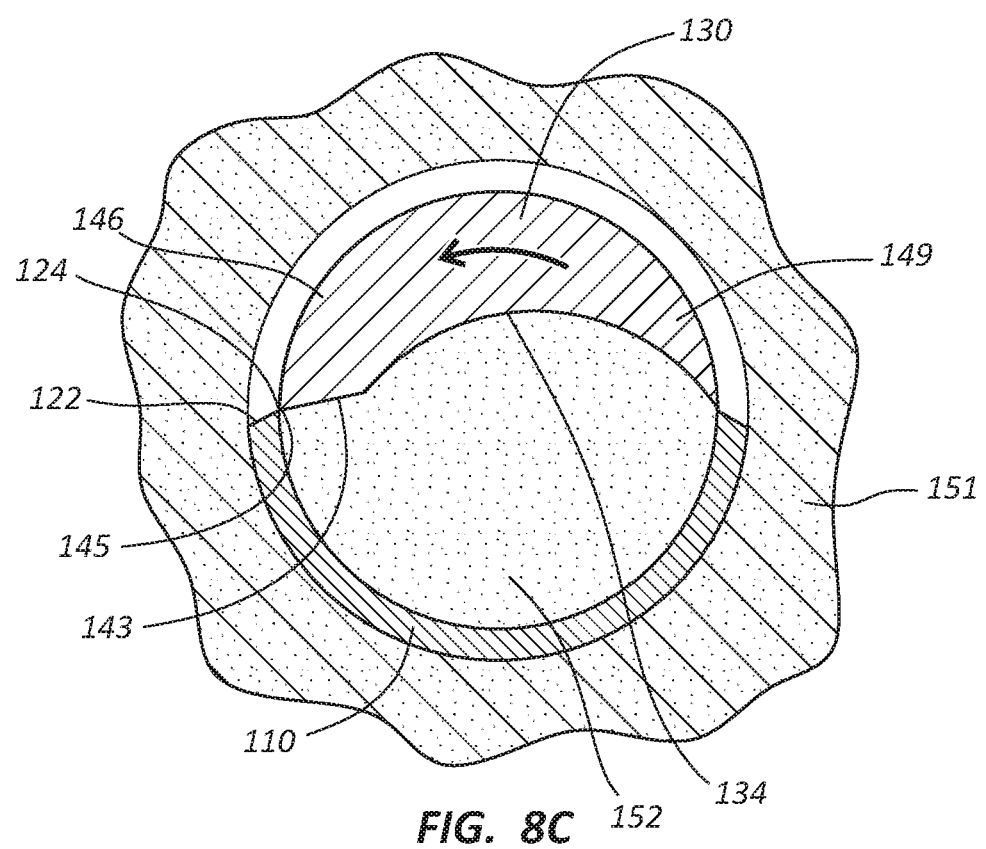
FIG. 8C is a schematic cross-sectional representation of the portions of the needle and the stylet of the biopsy needle assembly of FIG. 1 in a third configuration.

FIGS. 8A-8C are schematic in nature. In other words, the figures show the functional and operational relationships of a portion of the biopsy needle device 100 upon use in a patient, but the figures are not intended to indicate any particular structure or spatial disposition of any tissue, organ, body component, or group of body components in the patient. Additionally, the schematic representations herein may be drawn to show internal tissues and/or organs of the patient without explicitly designating cross-sections or cutaways of the tissues and/or organs. For example, a body tissue may be schematically shown with the biopsy needle assembly disposed therein without indicating a cross-section portion or cutaway of a portion of the body tissue. FIG. 8A is a schematic representation of a cross-sectional view of a portion of the biopsy needle device 100 of FIG. 1 in a first configuration. FIGS. 8B, and 8C are schematic representations of cross-sectional views of the portion of the needle device 100 of FIG. 1 in a second configuration and third configuration, respectively.

FIG. 8A illustrates portions of the needle 110 and the stylet 130 of the needle device 100 advanced into the target tissue or lesion 151 of a patient in a first configuration. In the configuration, needle window 113 may be closed or occluded by the stylet 130. The trough 134 of the stylet 130 may be oriented away from the window 113 such that trough 134 may not be exposed to the target tissue 151. FIG. 8B illustrates portions of the needle 110 and the stylet 130 in a second configuration. In the configuration of FIG. 8B, the stylet 130 may be rotated in the direction of the arrow, for example, a clockwise rotation, from the first configuration illustrated in FIG. 8A. Thus, the needle window 113 may be open and the trough 134 may be oriented toward the window 113. A tissue sample 152 may collapse or prolapse through the window 113 into the trough 134 such that tissue is disposed within the trough 134. In some embodiments, the trough 134 may be nearly filled with tissue. FIG. 8C illustrates portions of the needle and stylet in a third configuration. In the configuration of FIG. 8C, the stylet 130 may be rotated in the direction of the arrow, for example, a counter-clockwise rotation, from the second configuration illustrated in FIG. 8B. The needle window 113 may be closed and the trough 134 may be oriented away from the window 113. Due to the progression transition from the configuration of FIG. 8A to that of FIG. 8C, a tissue sample 152 may be cut or severed from the target tissue or lesion 151 and captured between the trough wall 141 and the needle wall 118.

Upon severing of the tissue sample 152, as illustrated in FIG. 8C, each of the stylet 130 and the needle 110 may be retracted from the body tissue 151 of the patient such that the tissue sample 152 may be extracted from the body tissue 151. In certain embodiments, the needle 110 may be maintained in position in the body tissue 151 and the stylet 130 may be substantially retracted from the needle 110 and body tissue 151.

Referring again to FIG. 1, in some embodiments, the biopsy needle device 100 may comprise a needle 110 and stylet 130 operatively coupled to a handle or actuator 150. For example, at least a portion of at least one of the proximal end portion 111 of the needle 110 and/or the proximal end portion 131 of the stylet 130 may be operatively coupled to the actuator 150. The actuator 150 may be configured to actuate at least one of the needle 110 and/or the stylet 130 to sever the tissue sample from the body of a patient. The actuator 150 may be configured to actuate the stylet 130 in a rotating motion relative the needle 110. In some embodiments, the activation may be triggered by two actions of the practitioner. For example, when the biopsy needle device may be prepped for use, the practitioner may cock the actuator 150. The cocking of the actuator 150 may cause the stylet 130 to be rotated 180 degrees in one direction to open the window 113 and to compress an activation mechanism such as a spring. The activation mechanism may lock in the cocked position. The practitioner may then wait for a period of time ranging from one second to five seconds to allow for the tissue sample 152 to collapse or prolapse through the window 113 into the trough 134. The practitioner may then activate the actuator 150. The spring of the activation mechanism may cause the stylet 130 to rotate approximately 180 degrees, in the opposite direction from the cocking rotation, relative to the needle window 113 resulting in cutting or severing of the tissue sample 152 from the surrounding tissue or lesion 151. The actuator 150 may also be configured to retract the needle 110 and stylet 130 from the body of a patient. The actuator 150 may include a mechanism that permits a manual reset of the actuation mechanism when additional tissues samples are desired. It is within the scope of this disclosure to couple components of the biopsy needle device 100, as described herein, to any type of handle or actuator 150. A handle or actuator 150 can have springs and can displace components of the biopsy needle device 100 relative to each other. Various handles or actuators may be used with the biopsy needle assemblies disclosed herein.

In some embodiments, an introducer cannula (not shown) may be used with the biopsy needle device 100 disclosed herein. The introducer cannula may comprise an outer cannula sized to permit passage of the biopsy needle 110, a trocar slidably disposed within the cannula and extending beyond the distal end of the cannula, and a depth stop to facilitate position of the introducer at the desired insertion depth. In use, the introducer cannula assembly may be inserted into a patient's tissue with the distal end of the cannula positioned adjacent to the targeted tissue 151. The depth stop may be used to restrict insertion depth to a predetermined depth. The trocar may be removed. The needle 110 and stylet 130 of the biopsy needle device 100 may be inserted through the introducer cannula and into the targeted tissue 151. A tissue sample 152 may be severed from the targeted tissue 151 and retained within the biopsy needle device 100. The biopsy needle device 100 may be withdrawn from the targeted tissue 151 and the introducer cannula. The tissue sample 152 may be extracted from the biopsy needle device 100. If additional tissue samples 152 are desired from the same target tissue 151, the process may be repeated. The introducer cannula may be removed from the patient when all desired tissue samples 152 have been collected.

The components of the present disclosure may be configured to minimize or eliminate translational impact of commonly used biopsy devices. Some biopsy devices may comprise a needle and a cutting stylet that are configured to translate axially into a target tissue of a patient. As such, a practitioner may advance the needle and stylet into a body tissue adjacent to the target tissue or lesion. The practitioner may then longitudinally advance components of the device to sever a sample. For example, rapid extension of a needle longitudinally over a previously extended stylet may cut or sever a sample tissue from the surrounding tissue. The longitudinal extension of the stylet and needle may be 2 to 3 cm (stroke length) and may be achieved via at least one spring mechanism within an actuator handle. The spring mechanism may cause rapid extension of the needle into the target tissue resulting in patient discomfort and potential undesired damage to surrounding tissue and/or organs.

In some instances, for example as described in the present disclosure, the structure and/or the form of the biopsy needle device 100 may be configured to minimize or eliminate a length (stroke length) of the device that rapidly penetrates tissue beyond the initial placement of the biopsy needle. As stated, embodiments of the biopsy needle device 100 of the current disclosure may be configured to minimize or eliminate translational movement of a portion of a biopsy needle during severing of a sample.

Minimizing or eliminating translational movement may increase the precision with which a practitioner can extract a tissue sample and thus limit unwanted trauma to tissue around the sample site. For example, in some instances, a practitioner may identify or locate a tissue sample for removal or extraction from a patient. The identified tissue sample, however, may be positioned at or adjacent to a body component, tissue, or organ that the practitioner may desire or need to avoid cutting, piercing, severing, etc. The body component may include, but is not limited to, a vessel. The biopsy needle assembly 100 of the present disclosure may be configured to minimize or eliminate translation movement may be utilized in such a circumstance or situation. At least a portion of a biopsy needle device 100, as disclosed herein, inserted into a patient and may be disposed within the target tissue to be sampled such that the window 113 and notch 133 are located at the targeted site. Confirmation may be achieved using imaging techniques such as ultrasound, magnetic resonance imaging, x-ray, fluoroscopy, etc. The practitioner may cock the actuator 150 resulting in a 180 degree rotation of the stylet 130 and opening of the needle window 113. Sample tissue 152 may collapse though the window 113 and into the trough 134. The practitioner may activate the actuator 150. The actuator may rotate the stylet 130 180 degrees in the direction opposite from the cocking rotation causing the knife edge 122 and the cutting edge 132 to cooperate to cut or sever the sample tissue 152 from the surrounding target tissue 151. The biopsy needle device may thus cut or sever without longitudinal translation of the needle and/or stylet. Therefore, the risk of cutting, piercing, or severing non-targeted body components, such as vessels, which may be positioned at or adjacent the target tissue may be minimized or reduced.

Without further elaboration, it is believed that one skilled in the art may use the preceding description to utilize the present disclosure to its fullest extent. The examples and embodiments disclosed herein are to be construed as merely illustrative and exemplary and not a limitation of the scope of the present disclosure in any way. It will be apparent to those having skill in the art, and having the benefit of this disclosure, that changes may be made to the details of the above-described embodiments without departing from the underlying principles of the disclosure herein.

The invention claimed is:

1. A biopsy needle assembly comprising:
a needle comprising a window; and
a stylet disposed within the needle comprising a notch, wherein the notch comprises:
  a closed distal end and a closed proximal end; and
  a cutting blade disposed between the closed distal end and the closed proximal end, comprising a bevel wherein the bevel comprises a surface angled downward from an outside surface of the stylet, wherein the surface comprises a decreasing width from a distal end to a proximal end of the bevel.

2. The biopsy needle assembly of claim 1, wherein the stylet is rotatably disposed within the needle.

3. The biopsy needle assembly of claim 1, wherein the cutting blade is inclined from a distal end to a proximal end of the cutting blade and wherein the angle of the incline is from one degree to three degrees.

4. The biopsy needle assembly of claim 1, wherein the window comprises at least one cutting edge.

5. The biopsy needle assembly of claim 4, wherein the cutting blade is configured to cooperate with the cutting edge such that a shear force severs a sample tissue.

6. The biopsy needle assembly of claim 1, wherein the stylet notch comprises a crescent shaped profile comprising a convex edge, a concave edge and two tips.

7. The biopsy needle assembly of claim 6, wherein the stylet notch further comprises a trough defined by the concave edge and configured to retain a tissue sample.

8. The biopsy needle assembly of claim 1, further comprising an actuator operably coupled to the needle and the stylet.

9. A biopsy needle assembly configured for use with a tissue biopsy device, the biopsy needle assembly comprising:
a needle comprising a window, wherein the window comprises a cutting edge; and
a stylet rotatably disposed within the needle, wherein the stylet comprises a notch configured to cooperate with the cutting edge to sever a tissue sample, wherein the notch comprises:
  a closed distal end and a closed proximal end;
  a crescent shaped transverse profile comprising a convex edge, a concave edge and two tips; and
  a cutting blade disposed between the closed distal end and the closed proximal end on at least one side of the notch structured at an incline from a distal end to a proximal end of the cutting blade, wherein the cutting blade comprises a bevel comprising:
    a surface angled downward from a horizontal plane disposed across the two tips and from an outside surface of the stylet; and
    a decreasing width from a distal end to a proximal end of the cutting blade.

10. The biopsy needle assembly of claim 9, wherein the notch further comprises a trough configured to retain the severed tissue sample.

11. The biopsy needle assembly of claim 9, wherein the stylet comprises a bullnose shaped distal end.

12. The biopsy needle assembly of claim 9, wherein the needle comprises a bevel configured to penetrate tissue.

13. The biopsy needle assembly of claim 12, wherein the needle bevel comprises a sharp tip and tissue cutting facets.

14. The biopsy needle assembly of claim 12, wherein the needle bevel is echogenic.

15. The biopsy needle assembly of claim 12, wherein the stylet comprises a distal end configured to match the contour of the needle bevel.

16. The biopsy needle assembly of claim 9, wherein the needle comprises at least one insertion depth indicium.

17. The biopsy needle assembly of claim 9, wherein the bevel surface is angled at from 25 degrees to 35 degrees relative to a horizontal plane disposed across the two tips.

18. A method of obtaining a tissue sample, comprising:
advancing a needle and a stylet into a body tissue utilizing a handle;
rotating the stylet in a first direction utilizing the handle, wherein the stylet comprises:
  a cutting blade comprising a bevel configured with a wide angled internal surface at a distal end and a narrow angled internal surface at a proximal end of the cutting blade; and
  a trough disposed such that the trough is opened to the window when the stylet is rotated in the first direction, wherein the trough comprises a closed distal end and a closed proximal end, and wherein the cutting blade is disposed between the closed distal end and the closed proximal end;
permitting a tissue sample of the body tissue to collapse through the window and into the opened trough;
rotating the stylet in a second direction with the handle such that the tissue sample is severed, the trough is closed to the window, and the tissue sample is retained within the trough; and
removing the needle and the stylet from the body tissue with the handle.

19. The method of claim 18, further comprising introducing the needle and the stylet into the body tissue utilizing an introducer.

20. The method of claim 18, further comprising:
leaving the needle in the body tissue;
retracting the stylet from the needle;
removing the tissue sample; and
re-inserting the stylet into the needle to retrieve a second tissue sample.

\* \* \* \* \*